(12) United States Patent
Neumann

(10) Patent No.: US 11,763,928 B2
(45) Date of Patent: Sep. 19, 2023

(54) SYSTEM AND METHOD FOR GENERATING A NEUROPATHOLOGIC NOURISHMENT PROGRAM

(71) Applicant: KPN INNOVATIONS, LLC., Lakewood, CO (US)

(72) Inventor: Kenneth Neumann, Lakewood, CO (US)

(73) Assignee: KPN INNOVATIONS, LLC., Lakewood, CO (US)

( * ) Notice: Subject to any disclaimer, the term of this patent is extended or adjusted under 35 U.S.C. 154(b) by 0 days.

(21) Appl. No.: 17/136,090

(22) Filed: Dec. 29, 2020

(65) Prior Publication Data

US 2022/0208338 A1 Jun. 30, 2022

(51) Int. Cl.

| | |
|---|---|
| *G16H 20/60* | (2018.01) |
| *G16H 50/20* | (2018.01) |
| *G16H 10/60* | (2018.01) |
| *G16H 40/67* | (2018.01) |
| *G16H 50/70* | (2018.01) |
| *A61B 5/00* | (2006.01) |

(Continued)

(52) U.S. Cl.
CPC ............. *G16H 20/60* (2018.01); *A61B 5/388* (2021.01); *A61B 5/7267* (2013.01); *G06N 3/04* (2013.01); *G16H 10/60* (2018.01); *G16H 40/67* (2018.01); *G16H 50/20* (2018.01); *G16H 50/70* (2018.01)

(58) Field of Classification Search
CPC ............................................... G06Q 50/22–26
See application file for complete search history.

(56) References Cited

U.S. PATENT DOCUMENTS

| | | |
|---|---|---|
| 7,187,790 B2 | 3/2007 | Sabol |
| 7,295,889 B2 | 11/2007 | Lahteenmaki |
| 9,710,606 B2 | 7/2017 | Apte |

(Continued)

FOREIGN PATENT DOCUMENTS

WO  2020069500 A1  4/2020

OTHER PUBLICATIONS

Deng et al., "Integrating Machine Learning with Human Knowledge" iScience 23, 101656, (Year: 2020).*

(Continued)

*Primary Examiner* — Neal Sereboff
(74) *Attorney, Agent, or Firm* — CALDWELL INTELLECTUAL PROPERTY LAW

(57) ABSTRACT

A system and method for generating a neuropathologic nourishment program comprises a computing device configured to obtain a neural element from a neural monitoring component, generate at least a neural profile as a function of the neural element, wherein generating comprises receiving at least a neural cluster as a function of a neural counsel, and generating the neural profile as a function of the neural cluster and neural element using a neural machine-learning model, identify at least an edible as a function of the neural profile, wherein identifying comprises obtaining a nourishment composition from an edible directory, determining a nourishment abnormality as a function of the neural profile and a normal range, and identifying an edible using the nourishment composition, nourishment abnormality, and an edible machine-learning model, and generate a nourishment program of a plurality of nourishment programs as a function of the edible.

16 Claims, 7 Drawing Sheets

(51) Int. Cl.
    *G06N 3/04*     (2023.01)
    *A61B 5/388*     (2021.01)

(56) References Cited

U.S. PATENT DOCUMENTS

| | | | |
|---|---|---|---|
| 9,936,916 B2 | 4/2018 | Sahin | |
| 10,327,641 B2 | 6/2019 | Apte | |
| 2012/0254196 A1* | 10/2012 | Abramski | G16H 20/60 707/748 |
| 2013/0158367 A1* | 6/2013 | Pacione | A61B 5/08 600/301 |
| 2014/0157171 A1* | 6/2014 | Brust | G06F 3/0481 715/771 |
| 2014/0221784 A1* | 8/2014 | Pacione | A61B 5/4866 600/300 |
| 2014/0347491 A1* | 11/2014 | Connor | A61B 5/1114 348/158 |
| 2015/0278442 A1* | 10/2015 | Rezaee | G16H 30/40 382/128 |
| 2019/0228856 A1* | 7/2019 | Leifer | G06F 16/9035 |
| 2019/0295440 A1* | 9/2019 | Hadad | G06F 40/295 |
| 2019/0304000 A1* | 10/2019 | Simpson | G16B 40/00 |
| 2020/0411185 A1* | 12/2020 | Oser | G16H 20/70 |

OTHER PUBLICATIONS

Lopez et al. "An unsupervised machine learning method for discovering patient clusters based on genetic signatures" Received Dec. 21, 2017; Received in revised form Jun. 22, 2018; Accepted Jul. 7, 2018 (Year: 2018).*

Islam et al., "An integrative deep learning framework for classifying molecular subtypes of breast cancer" https://doi.org/10.1016/j.csbj.2020.08.005 2001-0370/2020 (Year: 2020).*

Definition of "function" as downloaded from Google (Year: 2022).*

Karim et al., "Deep learning-based clustering approaches for bioinformatics" Briefings in Bioinformatics, 22(1), 2021, 393-415 (Year: 2020).* https://link.springer.com/article/10.1007/s10916-018-1071-x; Title: Machine learning for predicting cognitive diseases: methods, data sources and risk factors; By: Brati, Brankica; Date: Oct. 27, 2018.

https://www.mdpi.com/1422-0067/20/11/2842; Title: Frailty, cognitive decline, neurodegenerative diseases and nutrition interventions; By: Gomez-Gomez; Date: Jun. 11, 2019.

https://gsconlinepress.com/journals/gscbps/content/functional-foods-and-bioactive-compounds-roles-prevention-treatment-and-management; Title: Roles in the prevention, treatment and management of neurodegenerative diseases; By: Olagunj Abolaji.

https://www.tandfonline.com/doi/abs/10.1080/19390211.2017.1401573; Title: Functional foods and nutraceuticals as dietary intervention in chronic diseases; novel perspectives for health promotion and disease prevention; By: Adefegha, Stephen Adeniyi; Date: Dec. 27, 2017.

https://www.sciencedirect.com/science/article/pii/S0047637413001309; Title: Cognitive decline, dietary factors and gut-brain interactions; By: Caracciolo, Barbara; Date: Dec. 12, 2013.

https://www.ncbi.nlm.nih.gov/pmc/articles/PMC3975244/; Title: Neuroimaging biomarkers of neurodegenerative diseases and dementia; By: Shannon L. Risacher & Andrew J. Saykin; Date: Nov. 14, 2013.

https://www.sciencedirect.com/science/article/pii/S014067361630959X; Title: Diagnosis of multiple sclerosis: progress and challenges; By: Brownlee, Wallace J.; Date: Nov. 24, 2016.

https://www.ncbi.nlm.nih.gov/pmc/articles/PMC6150469/; Title: A novel dynamic hyper-graph inference framework for computer assisted diagnosis of neuro-diseases; By: Zhu, Yingying; Date: May 23, 2017.

https://dl.acm.org/doi/abs/10.1145/3344998; Title: Machine learning techniques for the diagnosis of Alzheimer's disease: A review; By: Tanveer, M.; Date: Apr. 1, 2020.

https://www.hindawi.com/journals/np/2017/3589271/; Title: Lifestyle modulators of neuroplasticity: how physical activity, mental engagement, and diet promote cognitive health during aging; By: Phillips, Christy; Date Jun. 12, 2017.

* cited by examiner

SYSTEM AND METHOD FOR GENERATING A NEUROPATHOLOGIC NOURISHMENT PROGRAM

FIELD OF THE INVENTION

The present invention generally relates to the field of artificial intelligence. In particular, the present invention is directed to a system and method for generating a neuropathologic nourishment program.

BACKGROUND

Current edible suggestion systems do not account for neural components of an individual. This leads to inefficiency of an edible suggestion system and a poor nutrition plan for the individual. This is further complicated by a lack of uniformity of nutritional plans, which results in dissatisfaction of individuals.

SUMMARY OF THE DISCLOSURE

In an aspect a system for generating a neuropathologic nourishment program comprises a computing device, the computing device configured to obtain a neural element from a neural monitoring component, generate at least a neural profile as a function of the neural element, wherein generating comprises receiving at least a neural cluster as a function of a neural counsel, and generating the neural profile as a function of the neural cluster and neural element using a neural machine-learning model, identify at least an edible as a function of the neural profile, wherein identifying comprises obtaining a nourishment composition from an edible directory, determining a nourishment abnormality as a function of the neural profile and a normal range, and identifying an edible using the nourishment composition, nourishment abnormality, and an edible machine-learning model, and output a nourishment program of a plurality of nourishment programs as a function of the edible.

In another aspect a method for generating a neuropathologic nourishment program comprises obtaining, by a computing device, a neural element from a neural monitoring component, generating, by the computing device, at least a neural profile as a function of the neural element, wherein generating comprises receiving at least a neural cluster as a function of a neural counsel, and generating the neural profile as a function of the neural cluster and neural element using a neural machine-learning model, identifying, by the computing device, at least an edible as a function of the neural profile, wherein identifying comprises obtaining a nourishment composition from an edible directory, determining a nourishment abnormality as a function of the neural profile and a normal range, and identifying an edible using the nourishment composition, nourishment abnormality, and an edible machine-learning model, and outputting, by the computing device, a nourishment program of a plurality of nourishment programs as a function of the edible.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for generating a neuropathologic nourishment program. In an embodiment, the disclosure may obtain a neural element from a neural monitoring component. Aspects of the present disclosure can be used to generate at least a neural profile as a function of the neural element using at least a neural cluster and a neural machine-learning model. Aspects of the present disclosure can also be used to identify at least an edible as a function of the neural profile. This is so, at least in part, because the edible is identified as a function of a nourishment composition, a nourishment abnormality, and an edible machine-learning model. Aspects of the present disclosure allow for outputting a nourishment program. Exemplary embodiments illustrating aspects of the present disclosure are described below in the context of several specific examples.

Figure 1:
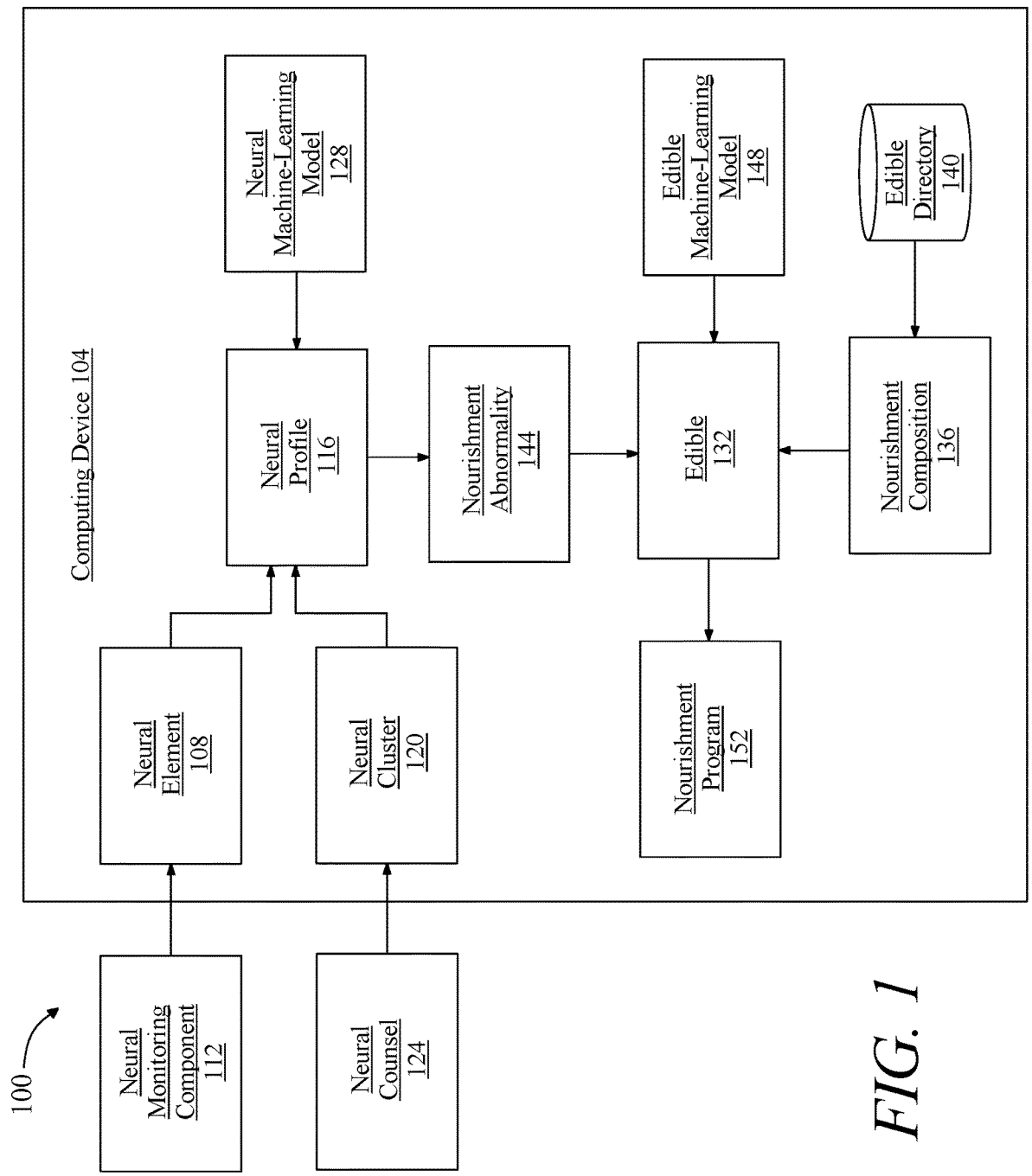
FIG. 1 is a block diagram illustrating an exemplary embodiment of a system for generating a neuropathologic nourishment program.

Referring now to FIG. 1, an exemplary embodiment of a system 100 for generating a neuropathologic nourishment program is illustrated. System includes a computing device 104. Computing device 104 may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. Computing device 104 may include a single computing device operating independently, or may include two or more computing device operating in concert, in parallel, sequentially or the like; two or more computing devices may be included together in a single computing device or in two or more computing devices. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Computing device 104 may include but is not limited to, for example, a computing device or cluster of computing devices in a first location and a second computing device or cluster of computing devices in a second location. Computing device 104 may include one or more computing devices dedicated to data storage, security, distribution of traffic for load balancing, and the like. Computing device 104 may distribute one or more computing tasks as described below across a plurality of computing devices of computing device, which may operate in parallel, in series, redundantly, or in any other manner used for distribution of tasks or memory between computing devices. Computing device 104 may be implemented using a "shared nothing" architecture in which data is cached at the worker, in an embodiment, this may enable scalability of system 100 and/or computing device.

With continued reference to FIG. 1, computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Still referring to FIG. 1 computing device 104 obtains a neural element 108. As used in this disclosure "neural element" an element that denotes an individual's nervous system health status. Neural element 108 may include a biological sample. As used in this disclosure "biological sample" is one or more biological specimens collected from an individual. Biological sample may include, without limitation, exhalate, blood, sputum, urine, saliva, feces, semen, and other bodily fluids, as well as tissue. Neural element 108 may include a neuron indicator. As used in this disclosure "neuron indicators" are one or more elements relating to the status of an individual's neuron. For example, and without limitation a neuron indicator may include an indicator and/or representation relating to a nerve's signal transduction, myeline sheath, synaptic vesicle formation, potassium gated channels, sodium gated channels, and the like thereof. Neural element 108 may include a glial indicator. As used in this disclosure "glial indicator" are one or more elements relating to the status of an individual's glial cells. As a non-limiting example, glial indicator may relate to a glial cell's guidance cues, neuron repair functions, myelin sheath formation, and the like thereof. Neural element 108 may include one or more biomarkers associated with the nervous system of an individual. As used in this disclosure "biomarker" is a chemical, marker, and/or gas that is associated with an individual's nervous system health status. As a non-limiting example, biomarker may include G-CIMP, N-methyl-D-aspartate receptor, D-dimmer, fibrinogen, fibronectin, von Willebrand factor, thrombomodulin, brain natriuretic peptide (BNP), lipoprotein-associated phospholipase A2, IL-6, TNF-alpha, tau proteins, amyloid B, dopamine metabolism, alpha synuclein, mitochondrial function, and the like thereof. Neural element 108 is obtained from a neural monitoring component 112, wherein a "neural monitoring component" is a component that relates to and/or represents an element associated with the status of an individual's nervous system as described in detail below, reference to FIG. 4. Neural monitoring component 112 may include one or more components that may perform laboratory screening tests and or genetic tests. Neural monitoring component 112 may include, without limitation, nervous system imaging devices. As a non-limiting example neural monitoring component may include a computed tomography scanning device, a magnetic resonance imaging device, a positron emission tomography scanning device, and/or a single photo emission computer tomography scanning device. As a further non-limiting example, neural monitoring component may collect, store, and/or calculate one or more lights, voltages, currents, sounds, chemicals, pressures, and the like thereof that are associated with an individual's nervous system.

Still referring to FIG. 1, computing device 104 may obtain neural element by receiving a neural assessment. As used in this disclosure "neural assessment" is an assessment of an individual's nervous system by an informed advisor. As a non-limiting example, neural assessment may include assessing an individual's mental status, cranial nerves, motor function, sensory function, pupillary response, reflexes, cerebral function, vital signs, and the like thereof. As a further non-limiting example neural assessment may include one or more assessments of level of consciousness, attention, orientation, language, memory, judgement, insight, reasoning, mood, and the like thereof. As used in this disclosure "informed advisor" is an individual that is skilled in a particular area relating to the study of neurology. As a non-limiting example an informed advisor may include a medical professional who may assist and/or participate in the medical treatment of an individual's nervous system including, but not limited to, neurologists, family physicians, medical geneticists, immunologists, internists, and the like thereof. An informed advisor may include a medical doctor, nurse, physician assistant, pharmacist, yoga instructor, nutritionist, spiritual healer, meditation teacher, fitness coach, health coach, life coach, and the like.

Still referring to FIG. 1, computing device 104 generates at least a neural profile 116 as a function of neural element 108. As used in this disclosure "neural profile" is a profile of a user's nervous system status. As a non-limiting example neural profile 116 may group neural elements of blinking, Babinski reflexes, startle reflex, plantar grasp, cranial nerve functions, coordination exams, and the like thereof. Computing device 104 may generate neural profile 116 by identifying at least a neural oddity as a function of neural element 108 and a neural threshold. As used in this disclosure "neural oddity" is an inadequacy and/or deviation of neural element 108. As a non-limiting example a neural oddity may exist due to a synaptic transmission rate of 245 mph, wherein a synaptic transmission rate should be 268 mph according to a neural threshold. As a further non-limiting example a neural oddity may exist due to a synaptic vesicle concentration of 295 mM, wherein a synaptic vesicle concentration should be 270 mM according to a neural threshold. As used in this disclosure "neural threshold" is a threshold a neural element should be. Neural threshold may be identified according to one or more medical guidelines for the measurement of nervous system function. As a non-limiting example a medical guideline for the measurement of nervous system function may include a defined threshold according to the National Institute of Neurological Disorders and Stroke, American Medical Association, American College of Physicians, and the like thereof. As a further non-limiting example, a medical guideline for the measurement of nervous system function may include a defined threshold according to one or more medical research journals, such as the Lancet, New England Journal of Medicine, Science, Journal of the American Medical Association, and the like thereof.

Still referring to FIG. 1, neural profile 116 is generated by receiving at least a neural cluster 120. As used in this disclosure "neural cluster" is one or more neural elements that are associated with a particular grouping of neural symptoms, as described below, in reference to FIG. 4. As a non-limiting example a neural cluster may include one or more groups associated with a central nervous system, peripheral nervous system, afferent division, efferent division, autonomic nervous system, somatic nervous system, sympathetic division, and/or parasympathetic division. Neural cluster 116 is received as a function of a neural counsel 124. As used in this disclosure "neural counsel" is one or more neurological reporters that at least identify a neural cluster. Neural counsel 124 may include one or more physicians, medical doctors, nurse practitioners, neurologists, and the like there of, as described above in detail. Neural counsel 124 may include one or more neurological research journals such as, but not limited to, Journal of Neurology, Neurology, Brain Research, Clinical Neurology and Neurosurgery, and the like thereof. As a non-limiting example neural counsel 124 may relate a neural element.

Still referring to FIG. 1, neural profile 116 is generated as a function of neural cluster 120, neural element 108 and a neural machine-learning model 128. As used in this disclosure "neural machine-learning model" is a machine-learning model to produce a neural profile given neural elements and neural clusters as inputs; this is in contrast to a non-machine learning software program where the commands to be executed are determined in advance by a user and written in a programming language. Neural machine-learning model 128 may include one or more neural machine-learning processes such as supervised, unsupervised, or reinforcement machine-learning processes that computing device 104 and/or a remote device may or may not use in the determination of neural profile 116. As used in this disclosure "remote device" is an external device to computing device 104. An neural machine-learning process may include, without limitation machine learning processes such as simple linear regression, multiple linear regression, polynomial regression, support vector regression, ridge regression, lasso regression, elasticnet regression, decision tree regression, random forest regression, logistic regression, logistic classification, K-nearest neighbors, support vector machines, kernel support vector machines, naïve bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, Markov decision processes, Deep Deterministic Policy Gradient (DDPG), or the like thereof.

Still referring to FIG. 1, computing device 104 may train neural machine-learning process 128 as a function of a neural training set. As used in this disclosure a "neural training set" is a training set that correlates at least neural cluster and neural element to a neural profile. For example, and without limitation, neural cluster of an autonomic nervous system and a neural element of visceral neuron synaptic transmission of 245 mph may relate to a neural profile of reduced visceral motor function. The neural training set may be received as a function of user-entered valuations of neural clusters, neural elements, and/or neural profiles. Computing device 104 may receive neural training set by receiving correlations of neural clusters and/or neural elements that were previously received and/or determined during a previous iteration of determining neural profiles. The neural training set may be received by one or more remote devices that at least correlate a neural cluster and neural element to a neural profile, wherein a remote device is an external device to computing device 104, as described above. The neural training set may be received by one or more user-entered correlations of neural clusters and neural elements to a neural profile. Additionally or alternatively, a user may include an informed advisor, wherein an informed advisor may include, without limitation, neurologists, family physicians, medical geneticists, immunologists, gastroenterologists, and the like thereof.

Still referring to FIG. 1, computing device 104 may receive neural machine-learning model 128 from the remote device that utilizes one or more neural machine learning processes, wherein a remote device is described above in detail. For example, and without limitation, a remote device may include a computing device, external device, processor, and the like thereof. The remote device may perform the neural machine-learning process using the neural training set to generate neural profile 116 and transmit the output to computing device 104. The remote device may transmit a signal, bit, datum, or parameter to computing device 104 that at least relates to neural profile 116. Additionally or alternatively, the remote device may provide an updated machine-learning model. For example, and without limitation, an updated machine-learning model may be comprised of a firmware update, a software update, an edible machine-learning process correction, and the like thereof. As a non-limiting example a software update may incorporate a neural cluster that relates to a modified neural element. Additionally or alternatively, the updated machine learning model may be transmitted to the remote device, wherein the remote device may replace the neural machine-learning model with the updated machine-learning model and determine the neural profile as a function of the neural cluster using the updated machine-learning model. The updated machine-learning model may be transmitted by the remote device and received by computing device 104 as a software update, firmware update, or corrected neural machine-learning model. For example, and without limitation a neural machine-learning model may utilize a principal component analysis machine-learning process, wherein the updated machine-learning model may incorporate kernel support vector machines machine-learning process. Updated machine learning model may additionally or alternatively include any machine-learning model used as an updated machine learning model as described in U.S. Nonprovisional application Ser. No. 17/106,658, filed on Nov. 30, 2020, and entitled "A SYSTEM AND METHOD FOR GENERATING A DYNAMIC WEIGHTED COMBINATION," the entirety of which is incorporated herein by reference.

Still referring to FIG. 1, computing device 104 identifies at least an edible 132 as a function of neural profile 116. As used in this disclosure an "edible" is a source of nourishment that may be consumed by a user such that the user may absorb the nutrients from the source. For example and without limitation, an edible may include legumes, plants, fungi, nuts, seeds, breads, dairy, eggs, meat, cereals, rice, seafood, desserts, dried foods, dumplings, pies, noodles, salads, stews, soups, sauces, sandwiches, and the like thereof. Computing device 104 identifies edible 132 as a function of obtaining a nourishment composition 136. As used in this disclosure "nourishment composition" is a list and/or compilation of all nutrients contained in an edible. As a non-limiting example nourishment composition 136 may include one or more quantities and/or amounts of total fat, including saturated fat and/or trans-fat, cholesterol, sodium, total carbohydrates, including dietary fiber and/or total sugars, protein, vitamin A, vitamin C, thiamin, riboflavin, niacin, pantothenic acid, vitamin b6, folate, biotin, vitamin B12, vitamin D, vitamin E, vitamin K, calcium, iron, phosphorous, iodine, magnesium, zinc, selenium, copper, manganese, chromium, molybdenum, chloride, and the like thereof. Nourishment composition 136 may be obtained as a function of an edible directory 140, wherein an edible directory is a database of edibles that may be identified as a function of one or more pulmonary bundle elements, as described in detail below, in reference to FIG. 3. Computing device 104 determines a nourishment abnormality 144 as a function of neural profile 116 and a normal range. As used in this disclosure "nourishment abnormality" is an abnormality and/or discrepancy of a nutrient in a user's body in relation to a normal range. As used in this disclosure "normal range" is a reference range and/or reference interval for a normal physiologic measurement of a nutrient in a healthy individual. As a non-limiting example neural profile 116 may determine a hemoglobin concentration of 9.7 g/dL, wherein a nourishment abnormality may be identified as low iron due to a normal range of 12.1-17.2 g/dL. As a further non-limiting example, neural profile 116 may determine a catecholamine production of 120 pg/mL of dopamine, wherein a nourishment abnormality may be identified as high dopamine due to a normal range of 0-30 pg/mL. Nourishment abnormality 144 may be identified according to one or more nourishment guidelines. As a non-limiting example a nourishment guideline may be identified according to a peer-review research journal, such as the Journal of Nutrition, Nutrition and Health, Advances in Nutrition, and the like thereof.

Still referring to FIG. 1, computing device 104 identifies edible 132 as a function of nourishment composition 136, nourishment abnormality 144, and an edible machine-learning model 148. As used in this disclosure "edible machine-learning model" is a machine-learning model to produce an edible output given nourishment compositions and nourishment abnormalities as inputs; this is in contrast to a non-machine learning software program where the commands to be executed are determined in advance by a user and written in a programming language. Edible machine-learning model 148 may include one or more edible machine-learning processes such as supervised, unsupervised, or reinforcement machine-learning processes that computing device 104 and/or a remote device may or may not use in the determination of edible 132. As used in this disclosure "remote device" is an external device to computing device 104. An edible machine-learning process may include, without limitation machine learning processes such as simple linear regression, multiple linear regression, polynomial regression, support vector regression, ridge regression, lasso regression, elasticnet regression, decision tree regression, random forest regression, logistic regression, logistic classification, K-nearest neighbors, support vector machines, kernel support vector machines, naïve bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, Markov decision processes, Deep Deterministic Policy Gradient (DDPG), or the like thereof.

Still referring to FIG. 1, computing device 104 may train edible machine-learning process 148 as a function of an edible training set. As used in this disclosure a "edible training set" is a training set that correlates at least nourishment composition and nourishment abnormality to an edible. For example, and without limitation, nourishment composition of 14 g of protein and 2 g of fiber and a nourishment abnormality of low levels of vitamin B12 as a function of Bell's palsy may relate to an edible of clams. The edible training set may be received as a function of user-entered valuations of nourishment compositions, nourishment abnormalities, and/or edibles. Computing device 104 may receive edible training by receiving correlations of nourishment compositions and/or nourishment abnormalities that were previously received and/or determined during a previous iteration of determining edibles. The edible training set may be received by one or more remote devices that at least correlate a nourishment composition and nourishment abnormality to an edible, wherein a remote device is an external device to computing device 104, as described above. The edible training set may be received by one or more user-entered correlations of a nourishment composition and nourishment abnormality to an edible. Additionally or alternatively, a user may include an informed advisor, wherein an informed advisor may include, without limitation, neurologists, family physicians, medical geneticists, immunologists, gastroenterologists, and the like thereof.

Still referring to FIG. 1, edible machine-learning model 148 may identify edible 132 as a function of one or more classifiers. A "classifier," as used in this disclosure is a machine-learning model, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Computing device 104 and/or another device may generate a classifier using a classification algorithm, defined as a processes whereby a computing device 104 derives a classifier from training data. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers.

Still referring to FIG. 1, computing device 104 may be configured to generate a classifier using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as $P(A/B)=P(B/A)P(A)\div P(B)$, where $P(AB)$ is the probability of hypothesis A given data B also known as posterior probability; $P(B/A)$ is the probability of data B given that the hypothesis A was true; $P(A)$ is the probability of hypothesis A being true regardless of data also known as prior probability of A; and $P(B)$ is the probability of the data regardless of the hypothesis. A naïve Bayes algorithm may be generated by first transforming training data into a frequency table. Computing device 104 may then calculate a likelihood table by calculating probabilities of different data entries and classification labels. Computing device 104 may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 1, computing device 104 may be configured to generate a classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 1, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least one value. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute/as derived using a Pythagorean norm: $l=\sqrt{\sum_{i=0}^{n} a_i^2}$, where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

Still referring to FIG. 1, computing device 104 may receive edible machine-learning model 148 from the remote device that utilizes one or more edible machine learning processes, wherein a remote device is described above in detail. For example, and without limitation, a remote device may include a computing device, external device, processor, and the like thereof. The remote device may perform the edible machine-learning process using the edible training set to generate edible 132 and transmit the output to computing device 104. The remote device may transmit a signal, bit, datum, or parameter to computing device 104 that at least relates to edible 132. Additionally or alternatively, the remote device may provide an updated machine-learning model. For example, and without limitation, an updated machine-learning model may be comprised of a firmware update, a software update, an edible machine-learning process correction, and the like thereof. As a non-limiting example a software update may incorporate a new nourishment composition that relates to a modified nourishment abnormality. Additionally or alternatively, the updated machine learning model may be transmitted to the remote device, wherein the remote device may replace the edible machine-learning model with the updated machine-learning model and determine the edible as a function of the nourishment abnormality using the updated machine-learning model. The updated machine-learning model may be transmitted by the remote device and received by computing device 104 as a software update, firmware update, or corrected edible machine-learning model. For example, and without limitation an edible machine-learning model may utilize a linear regression machine-learning process, wherein the updated machine-learning model may incorporate neural net machine-learning process. Updated machine learning model may additionally or alternatively include any machine-learning model used as an updated machine learning model as described in U.S. Nonprovisional application Ser. No. 17/106,658.

Still referring to FIG. 1, computing device 104 may identify edible 132 as a function of determining a neuropathologic disorder. As used in this disclosure "neuropathologic disorder" is an ailment and/or collection of ailments that impact an individual's nervous system. As a non-limiting example, neuropathologic disorders may include Alzheimer's disease, Bell's palsy, cerebral palsy, epilepsy, motor neuron disease, multiple sclerosis, neurofibromatosis, Parkinson's disease, peripheral neuropathies, seizure, central pontine myelinolysis, cerebral cavernous malformation, sarcoidosis, essential tremor, congenital toxoplasmosis, Tourette syndrome, and the like thereof. Neuropathologic disorder may be determined as a function of one or more neuropathologic machine-learning models. As used in this disclosure "neuropathologic machine-learning model" is a machine-learning model to produce a neuropathologic output given neural profiles as inputs; this is in contrast to a non-machine learning software program where the commands to be executed are determined in advance by a user and written in a programming language. Neuropathologic machine-learning model may include one or more neuropathologic machine-learning processes such as supervised, unsupervised, or reinforcement machine-learning processes that computing device 104 and/or a remote device may or may not use in the determination of neuropathologic disorder. As used in this disclosure "remote device" is an external device to computing device 104. A neuropathologic machine-learning process may include, without limitation machine learning processes such as simple linear regression, multiple linear regression, polynomial regression, support vector regression, ridge regression, lasso regression, elasticnet regression, decision tree regression, random forest regression, logistic regression, logistic classification, K-nearest neighbors, support vector machines, kernel support vector machines, naïve bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, Markov decision processes, Deep Deterministic Policy Gradient (DDPG), or the like thereof.

Still referring to FIG. 1, computing device 104 may train neuropathologic machine-learning process as a function of a neuropathologic training set. As used in this disclosure a "neuropathologic training set" is a training set that correlates at least neural enumeration and nervous system effect to a neuropathologic disorder. As used in this disclosure "neural enumeration" is a measurable value associated with the nervous system. As used in this disclosure "nervous system effect" is an impact and/or effect on the nervous system of an individual. As a non-limiting example a neural enumeration of 73 may be established for a nervous system effect of tingling sensations, wherein a neuropathologic disorder of multiple sclerosis may be determined. The neuropathologic training set may be received as a function of user-entered valuations of neural enumerations, nervous system effects, and/or neuropathologic disorders. Computing device 104 may receive neuropathologic training by receiving correlations of neural enumerations and/or neural effects that were previously received and/or determined during a previous iteration of determining neuropathologic disorders. The neuropathologic training set may be received by one or more remote devices that at least correlate a neural enumeration and/or nervous system effect to a neuropathologic disorder, wherein a remote device is an external device to computing device 104, as described above.

Still referring to FIG. 1, computing device 104 may receive neuropathologic machine-learning model from the remote device that utilizes one or more neuropathologic machine learning processes, wherein a remote device is described above in detail. For example, and without limitation, a remote device may include a computing device, external device, processor, and the like thereof. The remote device may perform the neuropathologic machine-learning process using the neuropathologic training set to generate neuropathologic disorder and transmit the output to computing device 104. The remote device may transmit a signal, bit, datum, or parameter to computing device 104 that at least relates to neuropathologic disorder. Additionally or alternatively, the remote device may provide an updated machine-learning model. For example, and without limitation, an updated machine-learning model may be comprised of a firmware update, a software update, a neuropathologic machine-learning process correction, and the like thereof. As a non-limiting example a software update may incorporate a new neural enumeration that relates to a modified nervous system effect. Additionally or alternatively, the updated machine learning model may be transmitted to the remote device, wherein the remote device may replace the neuropathologic machine-learning model with the updated machine-learning model and determine the neuropathologic disorder as a function of the neural enumeration using the updated machine-learning model. The updated machine-learning model may be transmitted by the remote device and received by computing device 104 as a software update, firmware update, or corrected neuropathologic machine-learning model. For example, and without limitation neuropathologic machine-learning model may utilize a Q-learning machine-learning process, wherein the updated machine-learning model may incorporate hierarchical clustering machine-learning process.

Still referring to FIG. 1, computing device 104 may identify edible as a function of a likelihood parameter. As used in this disclosure "likelihood parameter" is a parameter that identifies the probability of a user to consume an edible. As a non-limiting example likelihood parameter may identify a high probability that a user will consume an edible of steak. As a further non-limiting example likelihood parameter may identify a low probability that a user will consume an edible of cookies. Likelihood parameter may be determined as a function of a user taste profile. As used in this disclosure "user taste profile" is a profile of a user that identifies one or more desires, preferences, wishes, and/or wants that a user has. As a non-limiting example a user taste profile may include a user's preference for chicken flavor and/or crunchy textured edibles. Likelihood parameter may be determined as a function of an edible profile. As used in this disclosure "edible profile" is taste of an edible is the sensation of flavor perceived in the mouth and throat on contact with the edible. Edible profile may include one or more flavor variables. As used in this disclosure "flavor variable" is a variable associated with the distinctive taste of an edible, wherein a distinctive may include, without limitation sweet, bitter, sour, salty, umami, cool, and/or hot. Edible profile may be determined as a function of receiving flavor variable from a flavor directory. As used in this disclosure "flavor directory" is a database of flavors for an edible. As a non-limiting example flavor directory may include a list and/or collection of edibles that all contain umami flavor variables. As a further non-limiting example flavor directory may include a list and/or collection of edibles that all contain sour flavor variables. Likelihood parameter may alternatively or additionally include any user taste profile and/or edible profile used as a likelihood parameter as described in U.S. Nonprovisional application Ser. No. 17/032,080, filed on Sep. 25, 2020, and entitled "METHODS, SYSTEMS, AND DEVICES FOR GENERATING A REFRESHMENT INSTRUCTION SET BASED ON INDIVIDUAL PREFERENCES," the entirety of which is incorporated herein by reference.

Still referring to FIG. 1, computing device 104 outputs a nourishment program 152 of a plurality of nourishment programs as a function of the edible 132. As used in this disclosure "nourishment program" is a program consisting of one or more edibles that are to be consumed over a given time period, wherein a time period is a temporal measurement such as seconds, minutes, hours, days, weeks, months, years, and the like thereof. As a non-limiting example nourishment program 152 may consist of recommending steak for 3 days. As a further non-limiting example nourishment program 152 may recommend chicken for a first day, spaghetti for a second day, and mushrooms for a third day. Nourishment program 152 may include one or more diet programs such as paleo, keto, vegan, vegetarian, and the like thereof. Nourishment program 152 may be outputted as a function an intended outcome. As used in this disclosure "intended outcome" is an outcome that an edible may generate according to a predicted and/or purposeful plan. As a non-limiting example, intended outcome may include a treatment outcome. As used in this disclosure "treatment outcome" is an intended outcome that is designed to at least reverse and/or eliminate the effects of the neural profile and/or neuropathologic disorder. As a non-limiting example, a treatment outcome may include reversing the effects of the neuropathologic disorder abetalipoproteinemia. As a further non-limiting example, a treatment outcome includes reversing the neuropathologic disorder of microcephaly. Intended outcome may include a prevention outcome. As used in this disclosure "prevention outcome" is an intended outcome that is designed to at least prevent and/or avert a neural profile and/or neuropathologic disorder. As a non-limiting example, a prevention outcome may include preventing the development of the neuropathologic disorder Alzheimer's disease.

Still referring to FIG. 1, computing device 104 may output nourishment program 152 as a function of the intended outcome using a nourishment machine-learning model. As used in this disclosure "nourishment machine-learning model" is a machine-learning model to produce a nourishment program output given edibles and/or intended outcomes as inputs; this is in contrast to a non-machine learning software program where the commands to be executed are determined in advance by a user and written in a programming language. Nourishment machine-learning model may include one or more nourishment machine-learning processes such as supervised, unsupervised, or reinforcement machine-learning processes that computing device 104 and/or a remote device may or may not use in the output of nourishment program 152. As used in this disclosure "remote device" is an external device to computing device 104. Nourishment machine-learning process may include, without limitation machine learning processes such as simple linear regression, multiple linear regression, polynomial regression, support vector regression, ridge regression, lasso regression, elasticnet regression, decision tree regression, random forest regression, logistic regression, logistic classification, K-nearest neighbors, support vector machines, kernel support vector machines, naïve bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, Markov decision processes, Deep Deterministic Policy Gradient (DDPG), or the like thereof.

Still referring to FIG. 1, computing device 104 may train nourishment machine-learning process as a function of a nourishment training set. As used in this disclosure a "nourishment training set" is a training set that correlates an intended outcome to an edible. The nourishment training set may be received as a function of user-entered edibles, intendent outcomes, and/or nourishment programs. Computing device 104 may receive nourishment training by receiving correlations of intended outcomes and/or edibles that were previously received and/or determined during a previous iteration of outputting nourishment programs. The nourishment training set may be received by one or more remote devices that at least correlate an intended outcome and/or edible to a nourishment program, wherein a remote device is an external device to computing device 104, as described above.

Still referring to FIG. 1, computing device 104 may receive nourishment machine-learning model from the remote device that utilizes one or more nourishment machine learning processes, wherein a remote device is described above in detail. For example, and without limitation, a remote device may include a computing device, external device, processor, and the like thereof. The remote device may perform the nourishment machine-learning process using the nourishment training set to output nourishment program 152 and transmit the output to computing device 104. The remote device may transmit a signal, bit, datum, or parameter to computing device 104 that at least relates to nourishment program 152. Additionally or alternatively, the remote device may provide an updated machine-learning model. For example, and without limitation, an updated machine-learning model may be comprised of a firmware update, a software update, a nourishment machine-learning process correction, and the like thereof. As a non-limiting example a software update may incorporate a new intended outcome that relates to a modified edible. Additionally or alternatively, the updated machine learning model may be transmitted to the remote device, wherein the remote device may replace the nourishment machine-learning model with the updated machine-learning model and output the nourishment program as a function of the intended outcome using the updated machine-learning model. The updated machine-learning model may be transmitted by the remote device and received by computing device 104 as a software update, firmware update, or corrected nourishment machine-learning model. For example, and without limitation nourishment machine-learning model may utilize a nearest neighbor machine-learning process, wherein the updated machine-learning model may incorporate association rules machine-learning processes.

Figure 2:
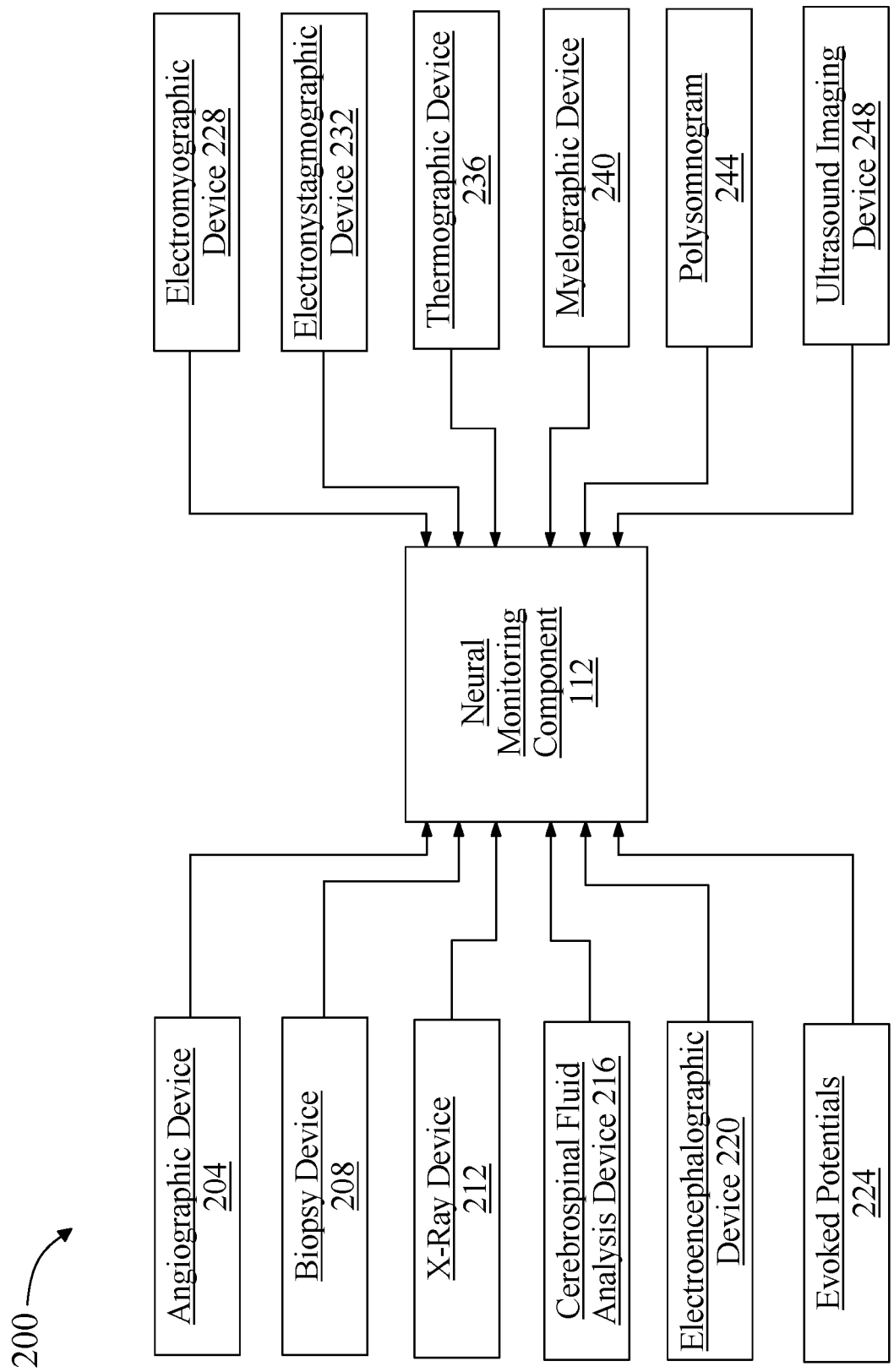
FIG. 2 is a block diagram of an exemplary embodiment of a neural monitoring component according to an embodiment of the invention.

Referring now to FIG. 2, an exemplary embodiment 200 of neural monitoring component 112 according to an embodiment of the invention is illustrated. Neural monitoring component 112 may include an angiography 204. As used in this disclosure "angiography" is a monitoring component that injects dye into the arteries and/or veins to detect a blockage and/or narrowing. As a non-limiting example, angiography 204 may include a cerebral angiogram that detects a narrowing and/or obstruction of blood vessel in the brain, head and/or neck of an individual. Neural monitoring component 112 may include a biopsy 208. As used in this this disclosure "biopsy" is a monitoring component that removes and/or examines a small piece of tissue from the individual. As a non-limiting example biopsy 208 may include a skin biopsy to measure small nerve fibers. Neural monitoring component 112 may include an x-ray 212. As used in this disclosure "x-ray" is a monitoring component that utilizes electromagnetic radiation to at least generate images of biological structures relating to the nervous system of an individual. As a non-limiting example x-ray 212 may include a fluoroscopy image of a lumbar puncture and/or clot of an individuals spinal cord. Neural monitoring component 112 may include a cerebrospinal fluid analysis 216. As used in this disclosure "cerebrospinal fluid analysis" is a monitoring component that removes a small amount of fluid that surrounds the brain and spinal cord of the individual. As a non-limiting example cerebrospinal fluid analysis 112 may include removing fluid surrounding the cervical spinal cord to detect evidence of brain hemorrhage, infection, multiple sclerosis, and/or other neurologic conditions. Neural monitoring component 112 may include an electroencephalographic device 220. As used in this disclosure "electroencephalographic device" is a monitoring component that measures the brain's electrical activity through the skull. As a non-limiting example electroencephalographic device 220 may include one or more electrical activity of the frontal lobe to monitor seizure disorders and/or sleep disorders. Neural monitoring component 112 may include an evoked potential 224. As used in this disclosure "evoked potential" is a monitoring component that measures the electrical signals to the brain generated by hearing, touch, sight. As a non-limiting example, evoked potential 224 may include an auditory evoked potential, visual evoked potential, somatosensory evoked potential, and the like thereof. Neural monitoring component 112 may include an electromyographic device 228. As used in this disclosure "electromyographic device" is a monitoring component that measures the electrical signals of muscles. As a non-limiting example, electromyographic device 228 may include a spinal nerve root compression. Neural monitoring component 112 may include an electronystagmographic device 232. As used in this disclosure "electronystagmographic device" is a monitoring component that measures the involuntary ocular movement, dizziness, and/or balance disorders. As a non-limiting example, electromyographic device 228 may include a person being tested wearing special goggles that help record the involuntary ocular movement. Neural monitoring component 112 may include a thermographic device 236. As used in this disclosure "thermographic device" is a monitoring component that uses digital infrared thermal imaging techniques to measure small thermal abnormalities between specific organs and/or nervous tissues. As a non-limiting example, thermographic device 236 may include a thermal image of a specific neuron and/or neuron nets. Neural monitoring component 112 may include a myelographic device 240. As used in this disclosure "myelographic device" is a monitoring component that uses contrast dye in the spinal canal. As a non-limiting example, myelographic device 236 may include injecting dye into an individual to diagnose herniated discs and/or spinal fractures. Neural monitoring component 112 may include a polysomnogram 244. As used in this disclosure "polysomnogram" is a monitoring component that measures brain and/or body activity during sleep. As a non-limiting example, polysomnogram 244 may include electrodes pasted and/or taped to an individual's scalp, eyelids, and/or chin to monitor various wake and/or sleep cycles of the individual. Neural monitoring component 112 may include an ultrasound imaging device 248. As used in this disclosure "ultrasound imaging device" is a monitoring component that uses high-frequency sound waves to obtain images inside the body. As a non-limiting example, ultrasound imaging device 248 may include a carotid doppler ultrasound, transcranial doppler ultrasound, and/or duplex ultrasound.

Figure 3:
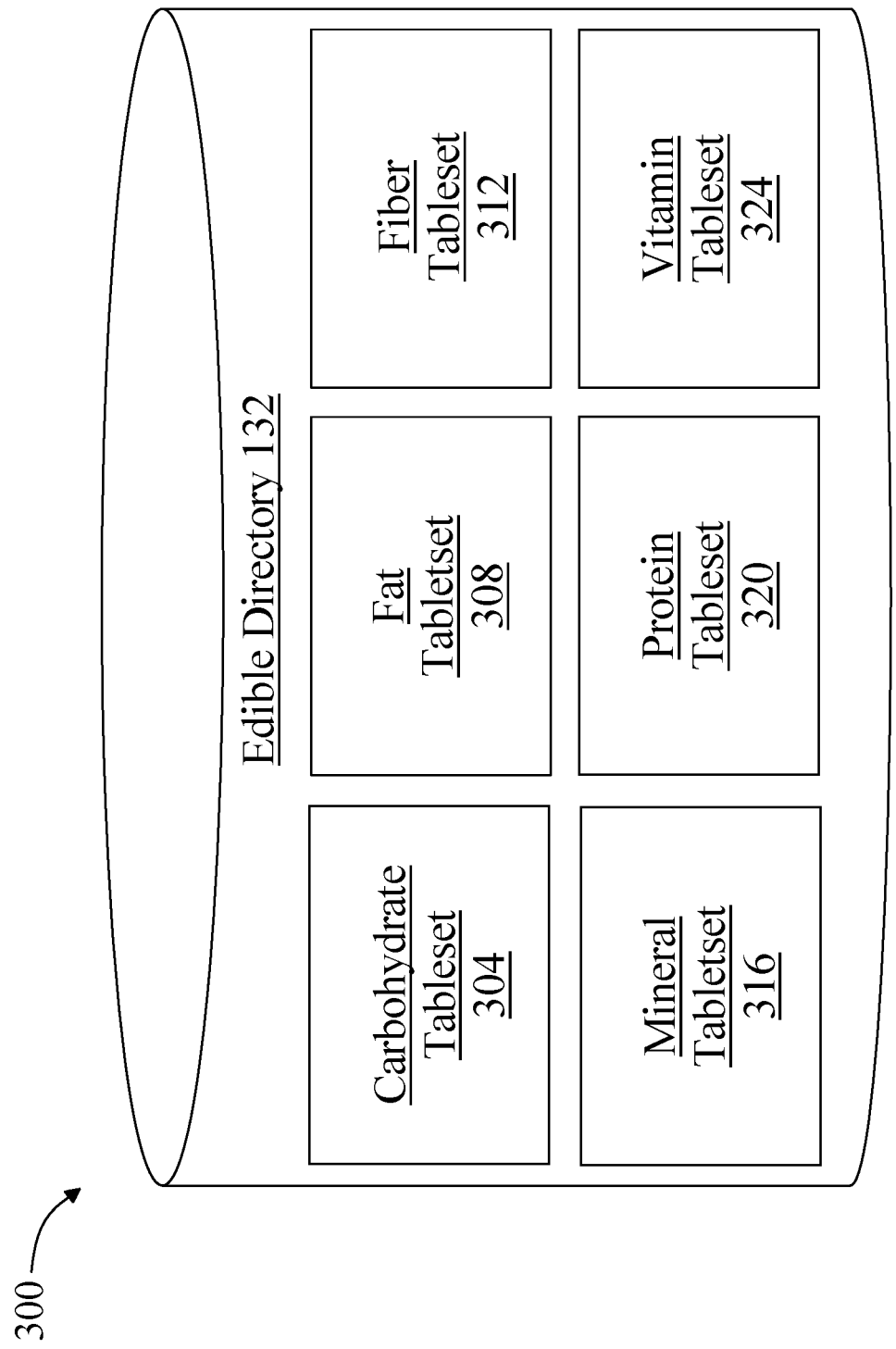
FIG. 3 is a block diagram of an exemplary embodiment of an edible directory according to an embodiment of the invention.

Now referring to FIG. 3, an exemplary embodiment 300 of an edible directory 140 according to an embodiment of the invention is illustrated. Edible directory 140 may be implemented, without limitation, as a relational databank, a key-value retrieval databank such as a NOSQL databank, or any other format or structure for use as a databank that a person skilled in the art would recognize as suitable upon review of the entirety of this disclosure. Edible directory 140 may alternatively or additionally be implemented using a distributed data storage protocol and/or data structure, such as a distributed hash table or the like. Edible directory 140 may include a plurality of data entries and/or records as described above. Data entries in a databank may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a databank may store, retrieve, organize, and/or reflect data and/or records as used herein, as well as categories and/or populations of data consistently with this disclosure. Edible directory 140 may include a carbohydrate tableset 304. Carbohydrate tableset 304 may relate to a nourishment composition of an edible with respect to the quantity and/or type of carbohydrates in the edible. As a non-limiting example, carbohydrate tableset 304 may include monosaccharides, disaccharides, oligosaccharides, polysaccharides, and the like thereof. Edible directory 132 may include a fat tableset 308. Fat tableset 308 may relate to a nourishment composition of an edible with respect to the quantity and/or type of esterified fatty acids in the edible. Fat tableset 308 may include, without limitation, triglycerides, monoglycerides, diglycerides, phospholipids, sterols, waxes, and free fatty acids. Edible directory 132 may include a fiber tableset 312. Fiber tableset 312 may relate to a nourishment composition of an edible with respect to the quantity and/or type of fiber in the edible. As a non-limiting example, fiber tableset 312 may include soluble fiber, such as beta-glucans, raw guar gum, *psyllium*, inulin, and the like thereof as well as insoluble fiber, such as wheat bran, cellulose, lignin, and the like thereof. Edible directory 132 may include a mineral tableset 316. Mineral tableset 316 may relate to a nourishment composition of an edible with respect to the quantity and/or type of minerals in the edible. As a non-limiting example, mineral tableset 316 may include calcium, phosphorous, magnesium, sodium, potassium, chloride, sulfur, iron, manganese, copper, iodine, zing, cobalt, fluoride, selenium, and the like thereof. Edible directory 132 may include a protein tableset 320. Protein tableset 320 may relate to a nourishment composition of an edible with respect to the quantity and/or type of proteins in the edible. As a non-limiting example, protein tableset 320 may include amino acids combinations, wherein amino acids may include, without limitation, alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, and the like thereof. Edible directory 132 may include a vitamin tableset 324. Vitamin tableset 324 may relate to a nourishment composition of an edible with respect to the quantity and/or type of vitamins in the edible. As a non-limiting example, vitamin tableset 324 may include vitamin A, vitamin $B_1$, vitamin $B_2$, vitamin $B_3$, vitamin $B_5$, vitamin $B_6$, vitamin $B_7$, vitamin $B_9$, vitamin $B_{12}$, vitamin C, vitamin D, vitamin E, vitamin K, and the like thereof.

Figure 4:
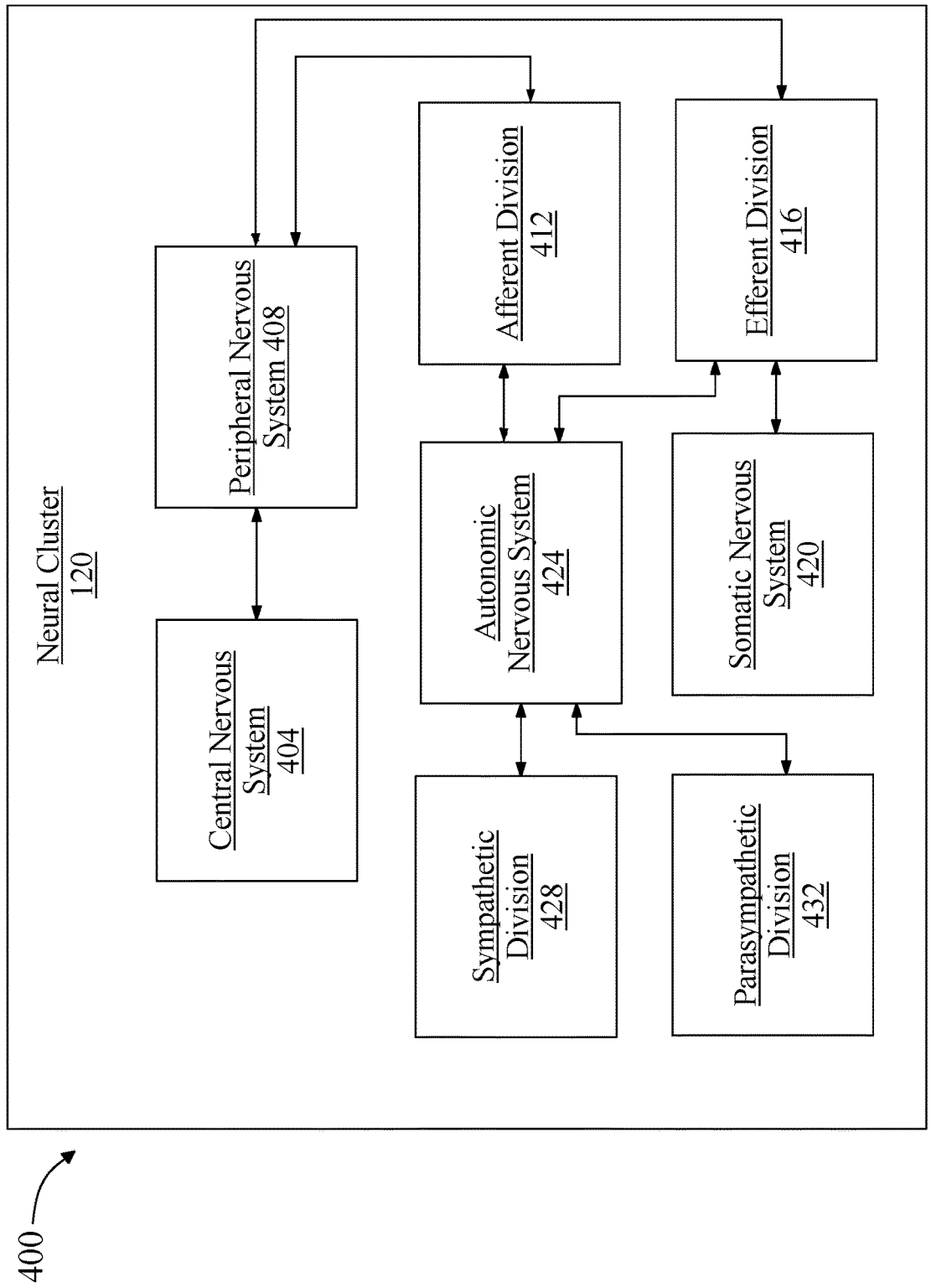
FIG. 4 is a block diagram of an exemplary embodiment of a neural cluster according to an embodiment of the invention.

Referring now to FIG. 4, an exemplary embodiment 400 of neural clustering 120 according to an embodiment of the invention is illustrated. Neural clustering 120 may include a cluster comprising a central nervous system 404. As used in this disclosure "central nervous system" is the part of the nervous system consisting of the brain and spinal cord. As a non-limiting example, central nervous system 404 may relate to the brainstem, cerebellum, diencephalon, cerebrum, and the like thereof. Central nervous system may transmit and/or receive nervous signals associated with a peripheral nervous system 408. As used in this disclosure "peripheral nervous system" is a cluster of nerves and/or ganglia that exist outside of the brain and spinal cord in an individual. As a non-limiting example peripheral nervous 408 may include thoracoabdominal nerves, lumbar plexus nerves, sacral plexus nerves, and brachial plexus nerves. Peripheral nervous system 412 may transmit and/or receive nervous signals associated with an afferent division 412. As used in this disclosure "afferent division" is a cluster of somatic and/or visceral sensory nerve fibers. As a non-limiting example afferent division 412 may conduct impulses from nerve receptors to peripheral nervous system 408. Peripheral nervous system 412 may transmit and/or receive nervous signals associated with an efferent division 416. As used in this disclosure "efferent division" is a cluster of motor nerve fibers. As a non-limiting example, efferent division 416 may conduct impulses from peripheral nervous system 408 to muscles and/or glands of the individual. Efferent division 416 may transmit and/or receive nervous signals associated with a somatic nervous system 420. As used in this disclosure "somatic nervous system" is a cluster of nerves associated with the voluntary control of body movements as a function of skeletal muscles. As a non-limiting example somatic nervous system 420 may include voluntary reflex arcs that at least release acetylcholine from alpha motor neurons to nicotinic acetylcholine receptors of muscles to voluntarily control muscle fibers. Efferent division 416 may transmit and/or receive nervous signals associated with an autonomic nervous system 424. As used in this disclosure "autonomic nervous system" is a cluster of nerves and/or ganglia that control bodily functions of an individual. As a non-limiting example autonomic nervous system 424 may include nervous signals that regulate heart rate, digestion, respiratory rate, pupillary response, urination, and/or sexual arousal. Autonomic nervous system 424 may transmit and/or receive nervous signals associated with a sympathetic division 428. As used in this disclosure "sympathetic division" is a cluster of nerves and/or ganglia associated with general visceral effects of an individual. As a non-limiting example sympathetic division 428 may include cells and/or cell bodies in the lateral grey column from T1 to L2/3 of the spinal cord of an individual. Autonomic nervous system 424 may transmit and/or receive nervous signals associated with a parasympathetic division 432. As used in this disclosure "parasympathetic division" is a cluster of nerves and/or ganglia associated with a craniosacral outflow, wherein a craniosacral outflow includes nerves originating as cranial nerves, spinal nerves, and/or pelvic splanchnic nerves. As a non-limiting example parasympathetic division 432 may include the oculomotor nerve, facial nerve, glossopharyngeal nerve, vagus nerve, and the like thereof.

Figure 5:
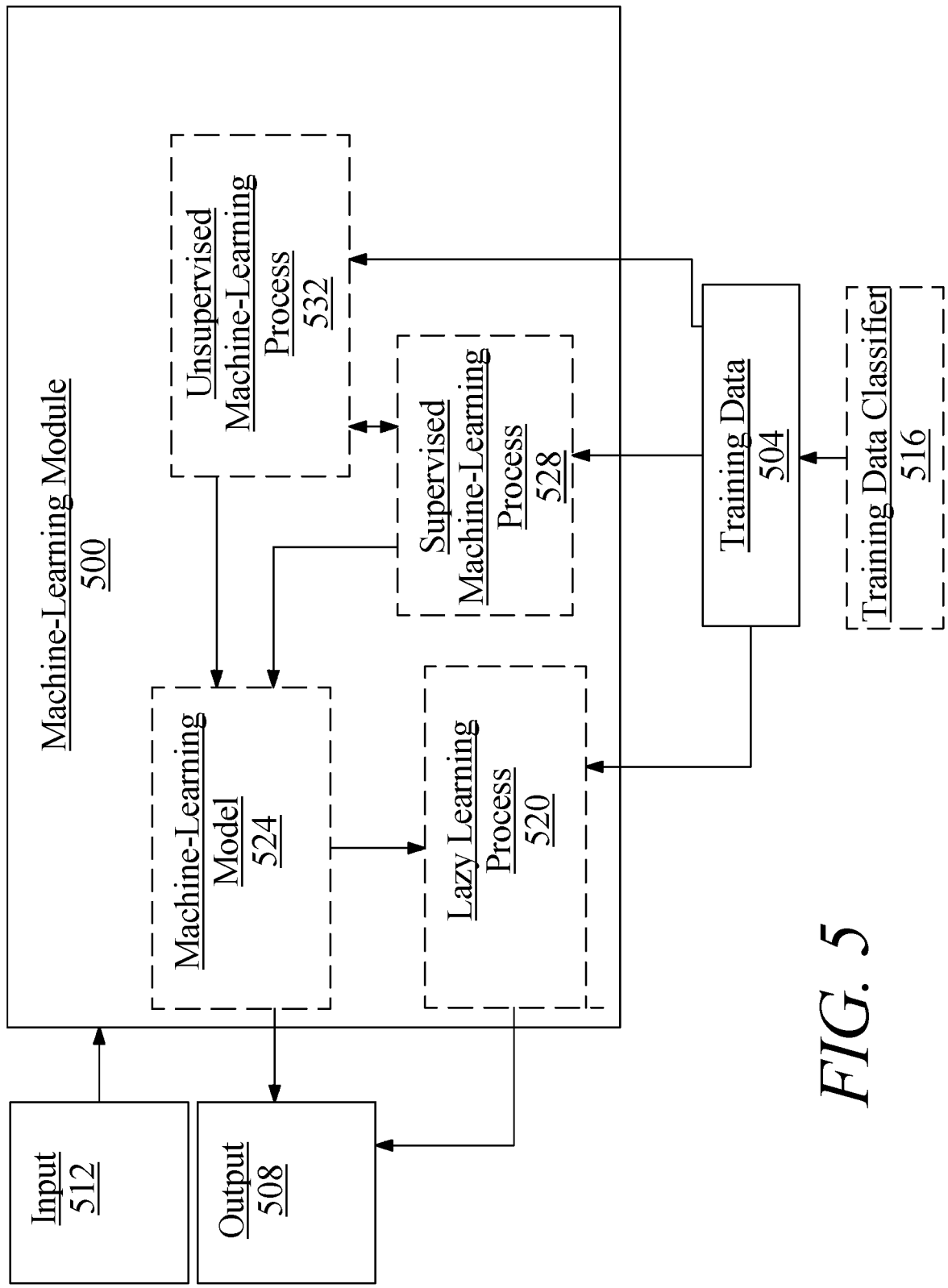
FIG. 5 is a block diagram of an exemplary embodiment of a machine-learning module.

Referring now to FIG. 5, an exemplary embodiment of a machine-learning module 500 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 504 to generate an algorithm that will be performed by a computing device/module to produce outputs 508 given data provided as inputs 512; this is in contrast to a non-machine learning software program where the commands to be executed are determined in advance by a user and written in a programming language.

Still referring to FIG. 5, "training data," as used herein, is data containing correlations that a machine-learning process may use to model relationships between two or more categories of data elements. For instance, and without limitation, training data 504 may include a plurality of data entries, each entry representing a set of data elements that were recorded, received, and/or generated together; data elements may be correlated by shared existence in a given data entry, by proximity in a given data entry, or the like. Multiple data entries in training data 504 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 504 according to various correlations; correlations may indicate causative and/or predictive links between categories of data elements, which may be modeled as relationships such as mathematical relationships by machine-learning processes as described in further detail below. Training data 504 may be formatted and/or organized by categories of data elements, for instance by associating data elements with one or more descriptors corresponding to categories of data elements. As a non-limiting example, training data 504 may include data entered in standardized forms by persons or processes, such that entry of a given data element in a given field in a form may be mapped to one or more descriptors of categories. Elements in training data 504 may be linked to descriptors of categories by tags, tokens, or other data elements; for instance, and without limitation, training data 504 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 5, training data 504 may include one or more elements that are not categorized; that is, training data 504 may not be formatted or contain descriptors for some elements of data. Machine-learning algorithms and/or other processes may sort training data 504 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 504 to be made applicable for two or more distinct machine-learning algorithms as described in further detail below. Training data 504 used by machine-learning module 500 may correlate any input data as described in this disclosure to any output data as described in this disclosure. As a non-limiting illustrative example neural clusters and neural elements as inputs and neural profiles as outputs.

Further referring to FIG. 5, training data may be filtered, sorted, and/or selected using one or more supervised and/or unsupervised machine-learning processes and/or models as described in further detail below; such models may include without limitation a training data classifier 516. Training data classifier 516 may include a "classifier," which as used in this disclosure is a machine-learning model as defined below, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 500 may generate a classifier using a classification algorithm, defined as a processes whereby a computing device and/or any module and/or component operating thereon derives a classifier from training data 504. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 516 may classify elements of training data to sub-categories of neural divisions, as described above in reference to FIG. 4.

Still referring to FIG. 5, machine-learning module 500 may be configured to perform a lazy-learning process 520 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 504. Heuristic may include selecting some number of highest-ranking associations and/or training data 504 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 5, machine-learning processes as described in this disclosure may be used to generate machine-learning models 524. A "machine-learning model," as used in this disclosure, is a mathematical and/or algorithmic representation of a relationship between inputs and outputs, as generated using any machine-learning process including without limitation any process as described above, and stored in memory; an input is submitted to a machine-learning model 524 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 524 may be generated by creating an artificial neural network, such as a convolutional neural network comprising an input layer of nodes, one or more intermediate layers, and an output layer of nodes. Connections between nodes may be created via the process of "training" the network, in which elements from a training data 504 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 5, machine-learning algorithms may include at least a supervised machine-learning process 528. At least a supervised machine-learning process 528, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include neural elements and/or neural clusters as described above as inputs, neural profiles as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 504. Persons skilled in the art, upon reviewing the entirety of this disclosure, will be aware of various possible variations of at least a supervised machine-learning process 528 that may be used to determine relation between inputs and outputs. Supervised machine-learning processes may include classification algorithms as defined above.

Further referring to FIG. 5, machine learning processes may include at least an unsupervised machine-learning processes 532. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 5, machine-learning module 500 may be designed and configured to create a machine-learning model 524 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 5, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Figure 6:
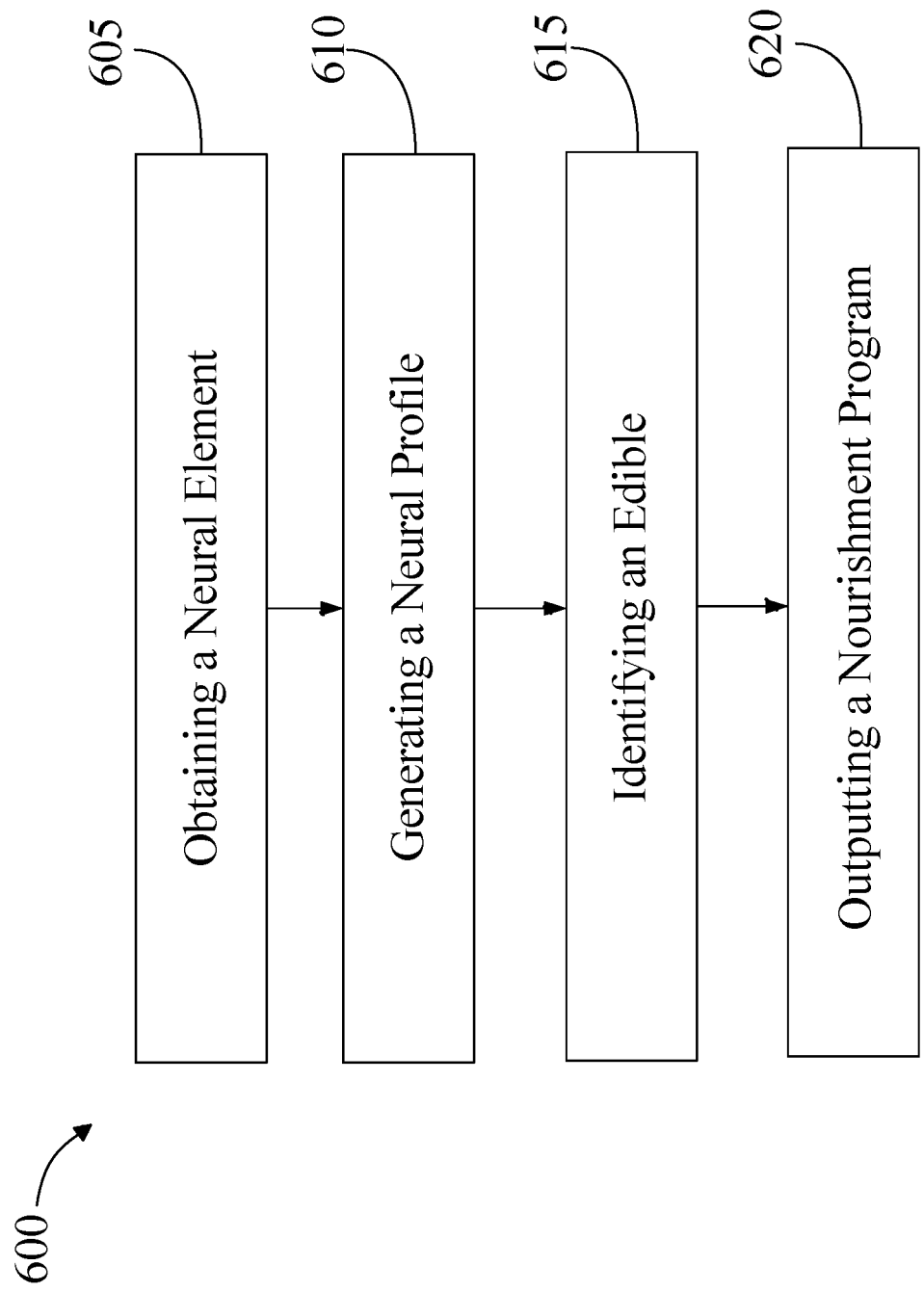
FIG. 6 is a process flow diagram illustrating an exemplary embodiment of a method of generating a neuropathologic nourishment program.

Now referring to FIG. 6, an exemplary embodiment of a method 600 for generating a neuropathologic nourishment program is illustrated. At step 605, a computing device 104 obtains a neural element 108 from a neural monitoring component 112. Computing device 104 includes any of the computing device 104 as described above, in reference to FIGS. 1-5. Neural element 108 Includes any of the neural element 108 As described above, in reference to FIGS. 1-5. Neural monitoring component 112 includes any of the neural monitoring component 112 as described above, in reference to FIGS. 1-5.

Still referring to FIG. 6, at step 610, computing device 104 generates at least a neural profile 116 as a function of neural element 108. Neural profile 116 includes any of the neural profile 116 as described above as described above, in reference to FIGS. 1-5. Computing device 104 generates neural profile 116 by receiving at least a neural cluster 120 as a function of a neural counsel 124. Neural cluster 120 includes any of the neural cluster as described above, in reference to FIGS. 1-5. Neural counsel 124 includes any of the neural counsel 124 as described above, in reference to FIGS. 1-5. Computing device 104 generates neural profile 116 as a function of neural cluster 120 and neural element 108 using a neural machine-learning model 128. Neural machine-learning model 128 includes any of the neural machine-learning model 128 as described above, in reference to FIGS. 1-5.

Still referring to FIG. 6, at step 615, computing device 104 identifies at least an edible 132 as a function of neural profile 116. Edible 132 includes any of the edible 132 as described above, in reference to FIGS. 1-5. Edible 132 is identified by obtaining a nourishment composition 136 from an edible directory 140. Nourishment composition 136 includes any of the nourishment composition 136 as described above in reference to FIGS. 1-5. Edible directory 140 includes any of the edible directory 140 as described above, in reference to FIGS. 1-5. Edible 132 is identified by determining a nourishment abnormality 144 as a function of neural profile 116 and a normal range. Nourishment abnormality 144 includes any of the nourishment abnormality 144 as described above, in reference to FIGS. 1-5. Edible 132 is identified using nourishment composition 136, nourishment abnormality 144, and an edible machine-learning model 148. Edible machine-learning model 148 includes any of the edible machine-learning model 148 as described above, in reference to FIGS. 1-5.

Still referring to FIG. 6, at step 620, computing device 104, outputs a nourishment program 152 of a plurality of nourishment programs as a function of edible 132. Nourishment program 152 includes any of the nourishment program 152 as described above, in reference to FIGS. 1-5.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 7:
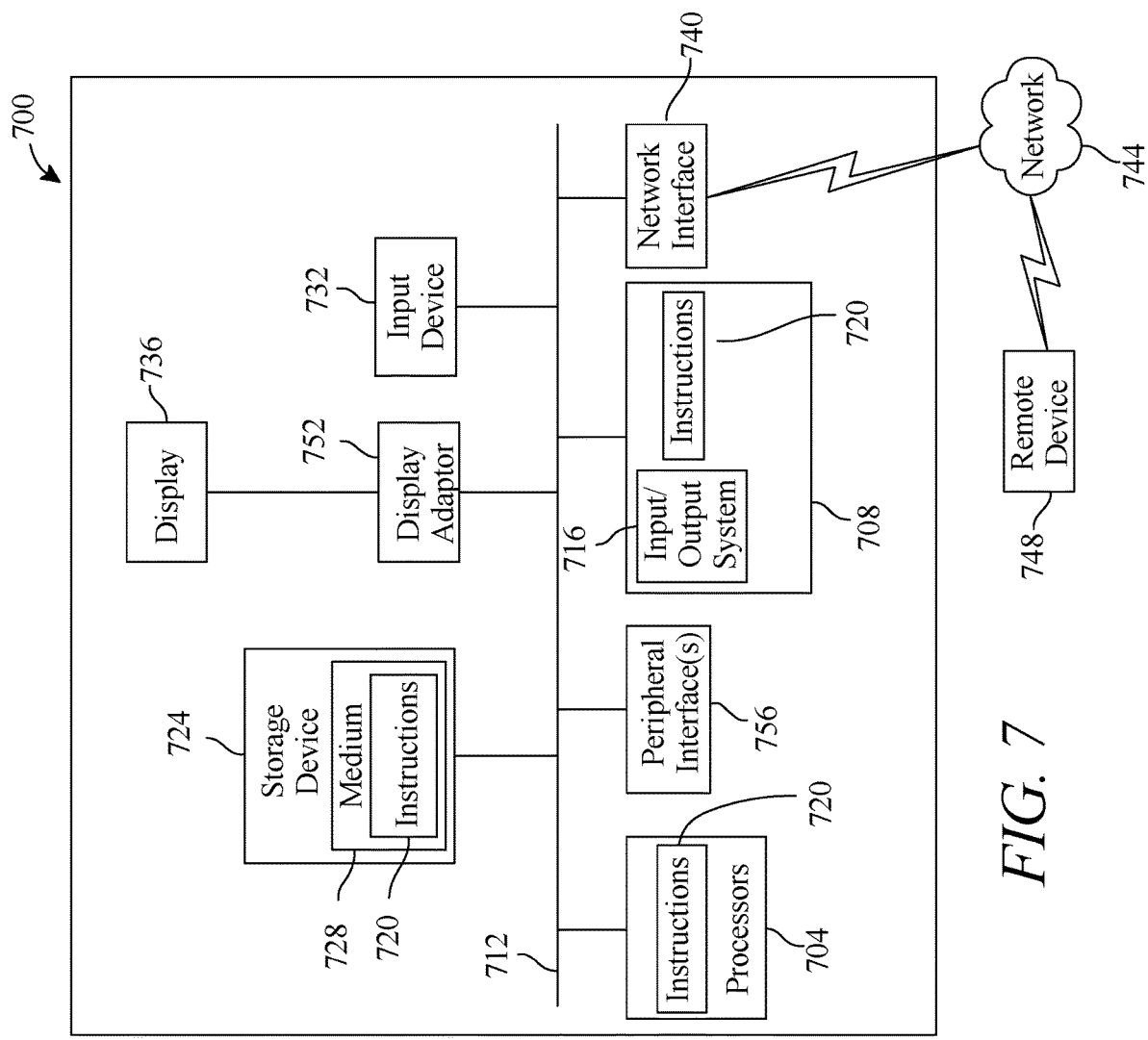
FIG. 7 is a block diagram of a computing system that can be used to implement any one or more of the methodologies disclosed herein and any one or more portions thereof.

FIG. 7 shows a diagrammatic representation of one embodiment of a computing device in the exemplary form of a computer system 700 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 700 includes a processor 704 and a memory 708 that communicate with each other, and with other components, via a bus 712. Bus 712 may include any of several types of bus structures including, but not limited to, a memory bus, a memory controller, a peripheral bus, a local bus, and any combinations thereof, using any of a variety of bus architectures.

Processor 704 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 704 may be organized according to Von Neumann and/or Harvard architecture as a non-limiting example. Processor 704 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC)

Memory 708 may include various components (e.g., machine-readable media) including, but not limited to, a random-access memory component, a read only component, and any combinations thereof. In one example, a basic input/output system 716 (BIOS), including basic routines that help to transfer information between elements within computer system 700, such as during start-up, may be stored in memory 708. Memory 708 may also include (e.g., stored on one or more machine-readable media) instructions (e.g., software) 720 embodying any one or more of the aspects and/or methodologies of the present disclosure. In another example, memory 708 may further include any number of program modules including, but not limited to, an operating system, one or more application programs, other program modules, program data, and any combinations thereof.

Computer system 700 may also include a storage device 724. Examples of a storage device (e.g., storage device 724) include, but are not limited to, a hard disk drive, a magnetic disk drive, an optical disc drive in combination with an optical medium, a solid-state memory device, and any combinations thereof. Storage device 724 may be connected to bus 712 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 724 (or one or more components thereof) may be removably interfaced with computer system 700 (e.g., via an external port connector (not shown)). Particularly, storage device 724 and an associated machine-readable medium 728 may provide nonvolatile and/or volatile storage of machine-readable instructions, data structures, program modules, and/or other data for computer system 700. In one example, software 720 may reside, completely or partially, within machine-readable medium 728. In another example, software 720 may reside, completely or partially, within processor 704.

Computer system 700 may also include an input device 732. In one example, a user of computer system 700 may enter commands and/or other information into computer system 700 via input device 732. Examples of an input device 732 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 732 may be interfaced to bus 712 via any of a variety of interfaces (not shown) including, but not limited to, a serial interface, a parallel interface, a game port, a USB interface, a FIREWIRE interface, a direct interface to bus 712, and any combinations thereof. Input device 732 may include a touch screen interface that may be a part of or separate from display 736, discussed further below. Input device 732 may be utilized as a user selection device for selecting one or more graphical representations in a graphical interface as described above.

A user may also input commands and/or other information to computer system 700 via storage device 724 (e.g., a removable disk drive, a flash drive, etc.) and/or network interface device 740. A network interface device, such as network interface device 740, may be utilized for connecting computer system 700 to one or more of a variety of networks, such as network 744, and one or more remote devices 748 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 744, may employ a wired and/or a wireless mode of communication. In general, any network topology may be used. Information (e.g., data, software 720, etc.) may be communicated to and/or from computer system 700 via network interface device 740.

Computer system 700 may further include a video display adapter 752 for communicating a displayable image to a display device, such as display device 736. Examples of a display device include, but are not limited to, a liquid crystal display (LCD), a cathode ray tube (CRT), a plasma display, a light emitting diode (LED) display, and any combinations thereof. Display adapter 752 and display device 736 may be utilized in combination with processor 704 to provide graphical representations of aspects of the present disclosure. In addition to a display device, computer system 700 may include one or more other peripheral output devices including, but not limited to, an audio speaker, a printer, and any combinations thereof. Such peripheral output devices may be connected to bus 712 via a peripheral interface 756. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve systems and methods according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for generating a neuropathologic nourishment program, the system comprising:
  a computing device, the computing device configured to:
    obtain a neural element from a neural monitoring component by receiving a neural assessment from at least an informed advisor, and obtaining the neural element as a function of the neural assessment, wherein the neural element includes a visceral neuron synaptic transmission speed;
    receive at least a neural cluster, wherein the at least a neural cluster is grouped with an autonomic nervous system;
    generate at least a neural profile as a function of the at least a neural cluster and the neural element using a neural machine-learning model, wherein the at least a neural profile includes a visceral motor function, wherein generating the at least a neural profile comprises:
      iteratively training the neural machine-learning model using a training set, wherein the training set correlates both neural clusters and neural elements to neural profiles including correlations determined during previous iterations of usage of determining neural profiles; and
      generating the at least a neural profile as a function of the at least a neural cluster and the neural element using the trained neural machine-learning model;
    identify at least an edible as a function of the at least a neural profile, wherein identifying the at least an edible comprises:
      obtaining a nourishment composition from a directory of edibles;
      determining a nourishment abnormality as a function of the at least a neural profile; and
      identifying an edible using the nourishment composition, nourishment abnormality, and an edible machine-learning model;
    output a nourishment metric as a function of the at least an edible;
    output a treatment outcome as a function of the at least an edible;
    determine a nourishment vector as a function of the nourishment metric; and
    generate a nourishment program as a function of the nourishment vector and the treatment outcome.

2. The system of claim 1, wherein the neural element includes a biomarker.

3. The system of claim 1, wherein identifying the at least an edible further comprises ascertaining a neuropathologic disorder as a function of the neural profile and identifying the at least an edible as a function of the neuropathologic disorder.

4. The system of claim 3, wherein ascertaining the neuropathologic disorder further comprises:
obtaining a neuropathologic training set; and
ascertaining the neuropathologic disorder using the neural profile and a neuropathologic machine-learning model, wherein the neuropathologic machine-learning model is trained as a function of the neuropathologic training set.

5. The system of claim 1, wherein determining the edible profile further comprises:
receiving a flavor variable from a flavor directory; and
ascertaining the edible profile as a function of the flavor variable.

6. The system of claim 1, wherein outputting the nourishment program further comprises:
retrieving an intended outcome; and
outputting the nourishment program as a function of the intended outcome using a nourishment machine-learning model.

7. The system of claim 6, wherein the intended outcome includes a treatment outcome.

8. The system of claim 6, wherein the intended outcome includes a prevention outcome.

9. A method for generating a neuropathologic nourishment program, the method comprising:
obtaining, by a computing device, a neural element from a neural monitoring component, including receiving a neural assessment from at least an informed advisor and obtaining the neural element as a function of the neural assessment, wherein the neural element includes a visceral neuron synaptic transmission speed;
receiving, by the computing device, at least a neural cluster, wherein the at least a neural cluster is part of an autonomic nervous system;
generating, by the computing device, at least a neural profile as a function of the at least a neural cluster and the neural element using a neural machine-learning model, wherein the at least a neural profile includes a visceral motor function profile, wherein generating the at least a neural profile further comprises:
iteratively training the neural machine-learning model using a training set, wherein the training set correlates both neural clusters and neural elements to neural profiles including correlations determined during previous iterations of usage of determining neural profiles; and
generating the at least a neural profile as a function of the at least a neural cluster and the neural element using the trained neural machine-learning model;
identifying, by the computing device, at least an edible as a function of the at least a neural profile, wherein identifying the at least an edible comprises:
obtaining a nourishment composition from a directory of edibles;
ascertaining a nourishment abnormality as a function of the at least a neural profile; and
identifying an edible using the nourishment composition, the nourishment abnormality, and an edible machine-learning model;
outputting, by the computing device, a nourishment metric as a function of the at least an edible;
outputting, by the computing device, a treatment outcome as a function of the at least an edible;
determining, by the computing device, a nourishment vector as a function of the nourishment metric; and
outputting, by the computing device, a nourishment program as a function of the nourishment vector and the treatment outcome.

10. The method of claim 9, wherein the neural element includes a biomarker.

11. The method of claim 9, wherein identifying the at least an edible further comprises ascertaining a neuropathologic disorder as a function of the neural profile and identifying the at least an edible as a function of the neuropathologic disorder.

12. The method of claim 11, wherein ascertaining the neuropathologic disorder further comprises:
obtaining a neuropathologic training set; and
determining the neuropathologic disorder using the neural profile and a neuropathologic machine-learning model, wherein the neuropathologic machine-learning model is trained as a function of the neuropathologic training set.

13. The method of claim 9, wherein identifying the edible further comprises:
receiving a flavor variable from a flavor directory; and
ascertaining the edible profile as a function of the flavor variable.

14. The method of claim 9, wherein outputting the nourishment program further comprises:
retrieving an intended outcome; and
outputting the nourishment program as a function of the intended outcome using a nourishment machine-learning model.

15. The method of claim 14, wherein the intended outcome includes a treatment outcome.

16. The method of claim 14, wherein the intended outcome includes a prevention outcome.

* * * * *